United States Patent
Mest

(10) Patent No.: US 6,564,096 B2
(45) Date of Patent: May 13, 2003

(54) METHOD AND SYSTEM FOR TREATMENT OF TACHYCARDIA AND FIBRILLATION

(76) Inventor: Robert A. Mest, 6102 Peabody St., Long Beach, CA (US) 90808

( * ) Notice: Subject to any disclaimer, the term of this patent is extended or adjusted under 35 U.S.C. 154(b) by 26 days.

(21) Appl. No.: 09/795,576

(22) Filed: Feb. 28, 2001

(65) Prior Publication Data

US 2002/0120304 A1 Aug. 29, 2002

(51) Int. Cl.$^7$ .................................................. A61N 1/368
(52) U.S. Cl. .................. 607/14; 607/99; 607/122; 607/113; 607/148
(58) Field of Search ..................... 607/1–9, 14–132, 607/148, 149, 154

(56) References Cited

U.S. PATENT DOCUMENTS

| | | | |
|---|---|---|---|
| 4,777,955 A | 10/1988 | Brayton et al. | 607/14 |
| 4,882,777 A | 11/1989 | Narula | 607/14 |
| 4,920,980 A | 5/1990 | Jackowski | 607/14 |
| 4,960,134 A | 10/1990 | Webster, Jr. | 607/14 |
| 4,984,581 A | 1/1991 | Stice | 607/14 |
| 5,170,787 A | 12/1992 | Lindegren | 607/14 |
| 5,255,679 A | 10/1993 | Imran | 607/14 |
| 5,263,493 A | 11/1993 | Avitall | 607/14 |
| 5,275,162 A | 1/1994 | Edwards et al. | 607/14 |
| 5,327,905 A | 7/1994 | Avitall | 607/14 |
| 5,354,297 A | 10/1994 | Avitall | 607/14 |
| 5,383,923 A | 1/1995 | Webster, Jr. | 607/14 |
| 5,411,531 A | 5/1995 | Hill et al. | 607/14 |
| 5,445,148 A | 8/1995 | Jaraczewski et al. | 607/14 |
| 5,466,245 A | 11/1995 | Spinelli et al. | 607/14 |
| 5,487,385 A | 1/1996 | Avitall | 607/14 |
| 5,492,119 A | 2/1996 | Abrams | 607/14 |
| 5,545,200 A | 8/1996 | West et al. | 607/14 |
| 5,549,581 A | 8/1996 | Lurie et al. | 607/14 |
| 5,582,609 A | 12/1996 | Swanson et al. | 607/14 |
| 5,617,854 A | 4/1997 | Munsif | 607/14 |
| 5,626,136 A | 5/1997 | Webster, Jr. | 607/14 |
| 5,642,736 A | 7/1997 | Avitall | 607/14 |
| 5,673,695 A | 10/1997 | McGee et al. | 607/14 |
| 5,680,860 A | 10/1997 | Imran | 607/14 |
| 5,700,282 A | 12/1997 | Zabara | 607/14 |
| 5,730,127 A | 3/1998 | Avitall | 607/14 |
| 5,755,760 A | 5/1998 | Maguire et al. | 607/14 |
| 5,772,590 A | 6/1998 | Webster, Jr. | 607/14 |
| 5,797,905 A | 8/1998 | Fleischman et al. | 607/14 |
| 5,800,428 A | 9/1998 | Nelson et al. | 607/14 |

(List continued on next page.)

FOREIGN PATENT DOCUMENTS

EP 0499491 A2 8/1992

OTHER PUBLICATIONS

Cooper et al., *Neural Effects on Sinus Rate and Atrioventricular Conduction Produced by Electrical Stimulation of a Transvenous Electrode Catheter in the Canine Right Pulmonary Artery*, Circulation Research, vol. 46, No. 1, Jan. 1980, pp. 48–57.

(List continued on next page.)

*Primary Examiner*—Mark Bockelman
*Assistant Examiner*—Jeanne Yu
(74) *Attorney, Agent, or Firm*—Christie, Parker & Hale, LLP

(57) ABSTRACT

A method for regulating the heart rate of a patient comprises inserting into a blood vessel of the patient a catheter having an electrode assembly at its distal end. The electrode assembly comprises a generally circular main region that is generally transverse to the axis of the catheter and on which is mounted at least one electrode. The catheter is directed to an intravascular location wherein the at least one electrode on the electrode assembly is adjacent a selected cardiac sympathetic or parasympathetic nerve. The at least one electrode is stabilized at the intravascular location. A stimulus is delivered through the at least one electrode, the stimulus being selected to stimulate the adjacent sympathetic or parasympathetic nerve to thereby cause a regulation of the patient's heart rate.

42 Claims, 6 Drawing Sheets

U.S. PATENT DOCUMENTS

| | | | |
|---|---|---|---|
| 5,827,278 A | 10/1998 | Webster, Jr. | 607/14 |
| 5,836,947 A | 11/1998 | Fleischman et al. | 607/14 |
| 5,860,920 A | 1/1999 | McGee et al. | 607/14 |
| 5,865,800 A | 2/1999 | Mirarchi et al. | 607/14 |
| 5,876,336 A | 3/1999 | Swanson et al. | 607/14 |
| 5,879,295 A | 3/1999 | Li et al. | 607/14 |
| 5,882,333 A | 3/1999 | Schaer et al. | 607/14 |
| 5,882,346 A | 3/1999 | Pomeranz et al. | 607/14 |
| 5,931,811 A | 8/1999 | Haissaguerre et al. | 607/14 |
| 5,935,102 A | 8/1999 | Bowden et al. | 607/14 |
| 5,938,694 A | 8/1999 | Jaraczewski et al. | 607/14 |
| 5,951,471 A | 9/1999 | de la Rama et al. | 607/14 |
| 5,984,909 A | 11/1999 | Lurie et al. | 607/14 |
| 5,997,526 A | 12/1999 | Giba et al. | 607/14 |
| 6,002,955 A | 12/1999 | Willems et al. | 607/14 |
| 6,035,224 A | 3/2000 | West | 607/14 |
| 6,064,902 A | 5/2000 | Haissaguerre et al. | 607/14 |
| 6,088,614 A | 7/2000 | Swanson | 607/14 |
| 6,090,104 A | 7/2000 | Webster, Jr. | 607/14 |
| 6,096,036 A | 8/2000 | Bowe et al. | 607/14 |
| 6,106,522 A | 8/2000 | Fleischman et al. | 607/14 |
| 6,129,724 A | 10/2000 | Fleischman et al. | 607/14 |
| 6,146,381 A | 11/2000 | Bowe et al. | 607/14 |
| 6,169,916 B1 | 1/2001 | West | 607/14 |
| 6,292,695 B1 | 9/2001 | Webster, Jr. et al. | 607/14 |

OTHER PUBLICATIONS

M. Haissaguerre et al., *Spontaneous Initiation of Atrial Fibrillation by Ectoic Beats Originating in the Pulmonary Veins*, The New England Journal of Medicine, 339:659–666 (Sep. 3), 1998.

Chiou, C.W., et al., *Efferent Vagal Innervation of the Canine Atria and Sinus and Atrioventricular Nodes*, Circulation 1997; 95:2573–2584.

Murphy, DA, et al., *Preliminary Observations on the Effects of the Stimulation of Cardiac Nerves in Man*, Can J Physiol Pharmacol 1995;63:649–655.

Schwartz et al., *Prevention of Sudden Cardiac Death After a First Myocardial Infarction by Pharmacologic or Surgical Antiadrenergic Interventions*, Journal of Cardiovascular Electrophysiology, vol. 3, No. 1, Feb. 1992, pp. 2–16.

Zipes, Douglas P., *Arrtythmogenic Role of Autonomic Innervation during Ischemia/Infarction and the Long QT Syndrome*, Journal of Cardiovascular Electrophysiology, vol. 2, No. 2, Supplement, Apr. 1991, pp. S92–S98.

Quan et al., *Endocardial Parasympathetic Nerve Stimulation Slows the Ventricular Rate During atrial Fibrillation in Humans*, PACE, vol. 19, No. 326, Apr. 1996, pp. 647.

Lazzara, R., et al., *Selective in Situ Parasympathetic Control of the Canine Sinoatrial and Atrioventricular Nodes*, Circulation Research, vol. 32, Mar. 1973; pp. 393–401.

Chen, SA, et al., *Intracardiac Stimulation of Human Parasympathetic Nerve Fibers Induces Negative Dromotroic Effects: Implication with the Lesions of Radiofreqency Catheter Ablation*,Cardiovasc Electrophysiol 1998;9:245–252.

Leenhardt, A., et al., *Catecholainergic Polymorphic Ventricular Tachycardia in Children*, American Heart Association, Circulation, vol. 91, No. 5, Mar. 1, 1995, pp. 1512–1519.

Stevenson, W.G., *Cardiac Sympathectomy to Prevent Sudden Death*, J. Cardiovasc Electrophysiol, vol. 3, pp. 17–20, Feb. 1992.

Armour, J.A., et al., *Gross and Microscopic Anatomy of the Human Intrinsic Cardiac Nervous System*, The Anatomical Record, 247:289–290 (1977).

Vanoli, E., et al., *Vagal Stimulation and Prevention of Sudden Death in Conscious Dogs with a Healed Myocardial Infarction*, Circulation Research, vol. 68, No. 5, May 1991, pp. 1471–1481.

Tsai, C., et al., *Bezold–Jarisch–Like Reflex During Radiofrequency Ablation of Pulmonary Vein Tissues in Patients with Paroxysmal Focal Atrial Fibrillation*, Journal of the Cardiovascular Electrophysiology, vol. 10, No. 1, Jan. 1999, pp. 27–35.

Scherlag, M.A., et al., *Transvenous Parasympathetic Cardiac Nerve Stimulation: A New Approach For Sinus Rate Control*, NASPE Abstracts, PACE, vol. 22, Apr. 1999, Part II, pp. 699.

Schauerte P.N., et al., *Atrial Fibrillation Initiated by Ectopic Beats Originating in the Pulmonary Veins and the Superior Vena Cava: Reproducible Induction by Cardiac Autonomic Nerve Stimulation*, NASPE Abstracts, PACE, vol. 22, Apr. 1999, Part II, p. 768.

Scherlag, B.J., et al., *Radiofrequency Ablation at the Junction of the Superior Vena Cava and Right Arium Terminates Neurally Induced Atrial Fibrillation*, NASPE Abstracts, PACE, vol. 22, Apr. 1999, Part II, p. 724.

Schauerte, P.N., *Ventricular Rate Control During Atrial Fibrillation by Cardiac Parasympathetic Nerve Stimulation: A Transvenous Approach*, NASPE Abstracts, PACE, vol. 22, Apr. 1999, Part II, p. 754.

Thompson, G. W., *Bradycardia Induced by Intravascular Versus Direct Stimulation of the Vagus Direct*, Ann Thorac Surg., 1998:65:637–42.

Shusterman, V., et al., *Autonomic Nervous System Activity and the Spontaneous Initiation of Ventricular Tachycardia*, JACC vol. 32, No. 7, Dec. 1998:1891–9.

METHOD AND SYSTEM FOR TREATMENT OF TACHYCARDIA AND FIBRILLATION

FIELD OF THE INVENTION

The present invention relates to an improved method and system for treating and controlling tachycardia and arrhythmias, and more particularly treating and controlling atrial fibrillation and ventricular tachycardia.

BACKGROUND OF THE INVENTION

Tachycardia is the rapid beating of the heart caused by abnormalities in any part of the heart, for example the atria, Purkinje system, or ventricles. Often the extremely rapid beating of the heart is uncoordinated and leads to fibrillation or flutter. These conditions occur after myocardial infarctions, for example, or in various pathological conditions, such as a dilated heart or blockage of the Purkinje system. The conditions can also occur following chemical therapies (e.g., epinephrine) or repetitive stimulation. Atrial flutter often becomes atrial fibrillation within a few days or weeks and leads to a complete failure of the atria to pump blood.

Atrial fibrillation is the most frequent tachycardia in patients. It most frequently occurs in patients over the age of 60 years and affects over 8% of patients with cardiovascular disease and people older than 80 years. Chronic atrial fibrillation doubles mortality, mostly due to an increased risk of stroke as well as other cardiovascular complications. Congestive heart disease imposes the highest risk for developing atrial fibrillation. Therefore, restoration of normal sinus rhythm by pharmacological or electrical cardioversion is attempted in many patients with atrial fibrillation. Unfortunately atrial fibrillation recurrence rates one year after successful cardioversion are high (75% without antiarrhythmic drug prophylaxis and 50% with aggressive antiarrhythmic medication). Moreover, the likelihood of cardioversion success is low in patients with chronic atrial fibrillation lasting longer than 2 years or in patients who have enlarged atria. In many of these patients, therapy is directed toward ventricular rate control during atrial fibrillation in order to stabilize cardiac function. However, in patients with concomitant heart failure, drugs that slow the ventricular rate during atrial fibrillation may further depress ventricular contractility and cause arterial hypotension or be of limited use due to side effects.

Like atrial fibrillation, ventricular tachycardia can lead to fibrillation, which leads to failure of the ventricles to pump blood. Unlike atrial fibrillation, ventricular fibrillation cannot be compensated for by the rest of the heart and rapidly leads to sudden death if not reversed. Ventricular fibrillation is a common cause of death in patients. For example, patients who survive myocardial infarction often remain at risk for reentrant ventricular tachycardia. The sympathetic and parasympathetic nerves (autonomic innervation) of the heart influence susceptibility to spontaneous arrhythmias. Sympathetic stimulation can increase the risk of fatal arrhythmias during ischemic events and parasympathetic stimulation can decrease the risk. Current efforts to control this excess sympathetic tone include administration of β-adrenergic blocking drugs and surgical sympathectomy. Problems with these methods include contraindications for drug therapy in patients who are sensitive to the negative inotropic effects of β-adrenergic blockade and the inherent risks of thoracic surgery, which in this case also include pulmonary complications, injury to the brachial plexus, and upper extremity paresthesias.

Another common measure used to control atrial or ventricular tachycardia is ablation or modification of the His bundle or atrioventricular node and ablation of atrial or ventricular foci. Such ablation may abolish a tachycardia or slow the ventricular response during atrial fibrillation by blocking impulse conduction across the atrioventricular node. Ablation can be performed by introduction of a catheter into the heart through the venous system and subsequent ablation of the tissue.

In 1973, Lazzara and Scherlag reported that electrical stimulation of parasympathetic cardiac nerves at the junction of the right atrium and the inferior vena cava close to the coronary sinus ostium selectively prolonged atrioventricular (AV) conduction time. (Lazzara R, Scherlag B J, Robinson M J et al. Selective in situ parasympathetic control of the canine sinuatrial and atrioventricular node. Circ Res 1973; 32:393–401.) Chen et al. showed control of ventricular rate during atrial fibrillation by short bursts of stimulation to parasympathetic nerves in the fat pads to the AV node. (Chen S A, Chiang C E, Tai C T et al. Intracardiac stimulation of human parasympathetic nerve fibers induces negative dromotropic effects: implication with the lesions of radio frequency catheter ablation. Cardiovasc. Electrophysiol. 1998;9: 245–252.) However, this method can lead to unwanted stimulation of myocardial muscle, and stimulation times are necessarily very brief because the electrode cannot be stably maintained in the appropriate location. More recently, Reek et al. reported that stimulation of the parasympathetic nerve fibers in the RPA with a conventional electrode catheter decreased the sinus rate in sheep. (Reek S, Geller J C, Hartung W M, Auricchio A. Einfluss transvenöser elektrischer Stimulation in der rechten Pulmonalarterie auf Sinusknotenläre und ventrikuläre Refrakt ärzeiten. Z Kardiologie 1999;88, Suppl. 1:10.) In addition, electrical stimulation of parasympathetic nerves either during or after coronary artery bypass grafting operation have demonstrated that parasympathetic fibers innervating the sinus and atrioventricular node can also be stimulated in humans. (Murphy D A, Johnstone D E, Armour J A. Preliminary observations on the effects of stimulation of cardiac nerves in man. Can J Physiol. Pharmacol. 1985;63:649–655; Quan K J, Mackall J A, Biblo L A, Van Hare G F, Carlson M d. Endocardial parasympathic stimulation slows the ventricular rate during atrial fibrillation in humans. PACE 1996;19:647 (abstract).) The stimulation electrodes, however, were only temporarily fixed at the outer surface of the heart or superior vena cava. Chiou et al. demonstrated that extracardiac electrical stimulation of parasympathetic fibers in fat pad between the superior vena cava, the aorta, and adjacent to the right pulmonary artery, diminished AV nodal conduction during sinus rhythm. (Chiou C W, Eble J N, Zipes D P. Efferent vagal innervation of the canine atria and sinus and atrioventricular nodes. Circulation 1997;95:2573–2584.) These results required a thoracotomy. Additionally, Thompson and coworker reported that endovascular electrical stimulation of parasympathetic fibers in the superior vena cava with a conventional electrode catheter slows the sinus rate. (Thompson G W, Levett J M, Miller S M et al. Bradycardia induced by intravascular versus direct stimulation of the vagus nerve. Ann Thorac Surg 1998;65(3):637–42.)

Copending application Ser. No. 09/334,822, entitled Method and Apparatus for Transvascular Treatment of Tachycardia and Fibrillation, discloses the use of a catheter having an expandable basket-shaped electrode array for delivering a stimulus adjacent to one or more predetermined cardiac parasympathetic nerves to slow or regulate the beating rate of the heart. The basket-shaped electrode array provides excellent stability during stimulation.

SUMMARY OF THE INVENTION

The present invention is directed to an improved method and system for controlling the heart rate of a patient and is particularly useful in controlling cardiac fibrillation and tachycardia. The method involves the intravascular stimulation and/or ablation of cardiac parasympathetic and sympathetic nerves sufficient to regulate or slow the heart rate or prevent the occurrence of these arrhythmias. In connection with the method and system, an improved catheter is provided having a generally circular electrode array that is generally transverse to the axis of the catheter. This improved design is smaller and less cumbersome than the basket-shaped electrode array, described above, and reduces the risk of clotting.

In one embodiment, the invention is directed to a method for regulating the heart rate of a patient. The method comprises inserting into a blood vessel of the patient a catheter having an electrode assembly at its distal end. The electrode assembly comprises a generally circular main region that is generally transverse to the axis of the catheter and on which is mounted at least one electrode. The catheter is directed to an intravascular location wherein the electrode on the electrode assembly is adjacent a selected cardiac sympathetic or parasympathetic nerve. The electrode is stabilized at the intravascular location, and a stimulus is delivered through the electrode. The stimulus is selected to stimulate the adjacent sympathetic or parasympathetic nerve to thereby cause a regulation of the patient's heart rate.

In another embodiment, the invention is directed to a method of selectively ablating a sympathetic or parasympathetic innervation of at least one portion of the heart of a patient. The method comprises inserting into a blood vessel of the patient a catheter having an electrode assembly at its distal end. The electrode assembly comprises a generally circular main region that is generally transverse to the axis of the catheter and on which is mounted at least one electrode. The catheter is directed to an intravascular location wherein the electrode on the electrode assembly is adjacent a selected cardiac sympathetic or parasympathetic nerve. The electrode is stabilized at the intravascular location, and an ablation stimulus is delivered through the electrode. The ablating stimulus is sufficient to damage the nerve so that it no longer conducts impulses to the heart.

In another embodiment, the invention is directed to a system to regulate the heart rate of a patient. The system comprises a catheter having an electrode assembly at its distal end. The electrode assembly comprises a generally circular main region that is generally transverse to the axis of the catheter and on which is mounted at least one electrode. The system further comprises a signal generator electrically connected to the at least one electrode on the generally circular main region. The signal generator is capable of generating stimulating pulses having a frequency of from about 1 Hz to about 200 Hz, an intensity of from about 1 V to about 200 V and a duration of from about 0.01 msec to about 10 msec.

DESCRIPTION OF THE DRAWINGS

These and other features and advantages of the present invention will be better understood by reference to the following detailed description when considered in conjunction with the accompanying drawings wherein.

DETAILED DESCRIPTION

The present invention provides a system comprising a minimally invasive catheter and low frequency signal generator for treating and preventing atrial and ventricular tachycardia and cardiac arrhythmias by specific stimulation of parasympathetic or sympathetic nerves innervating the heart. The invention also provides a system comprising a minimally invasive catheter and an ablation signal generator for treating and preventing tachycardia by specific ablation of parasympathetic and/or sympathetic nerves innervating the heart. As used herein, "tachycardia" means the rapid beating of the heart, and can include fibrillation and flutter. "Fibrillation" means an uncoordinated contraction of cardiac muscle, leading to inefficient pumping of the heart. "Flutter" means an extremely rapid beating.

Figure 1:
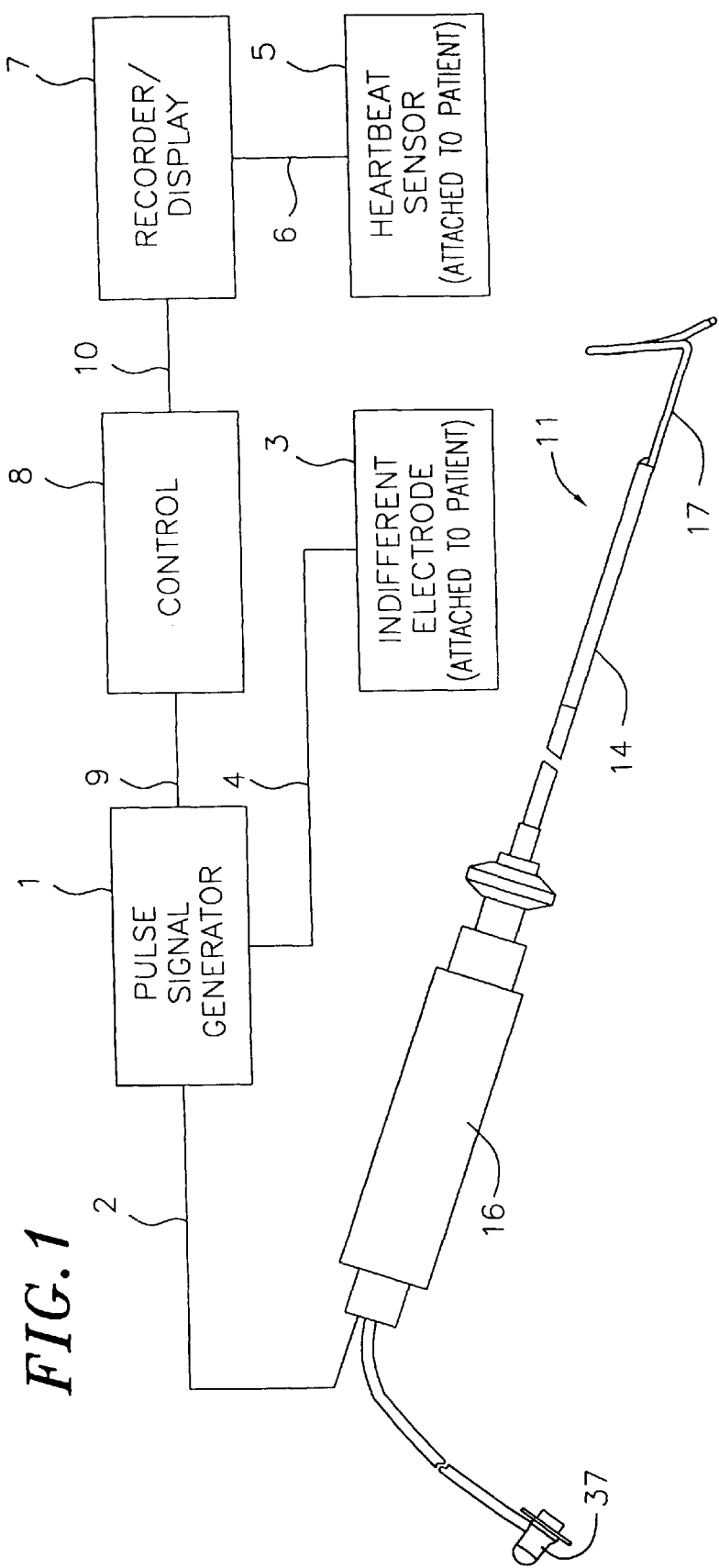
FIG. 1 is a schematic view of a preferred system for regulating the heart rate of a patient in accordance with the invention.

A preferred system in accordance with the present invention is shown in FIG. 1. The system comprises a steerable catheter 11, having a generally circular electrode assembly 17 at its distal end. The electrode assembly 17 carries a plurality of electrodes 36 that are electrically connected to a signal generator 1 (e.g., a pulse signal generator) by electrode lead wires 50 that extend through the interior of the catheter 10 and an electrical connection 2. One or more indifferent electrodes 3, which are placed on the patient's skin, are also electrically connected to the signal generator 1 by an electrical connection 4. Preferably the signal generator 1 is capable of generating a signal having a frequency from about 1 to about 200 Hz, more preferably from about 20 to about 30 Hz, an intensity of from about 1 to about 150 volts, more preferably from about 8 to about 15 volts, and a pulse duration of from about 1 microsecond to about 10 milliseconds, more preferably from about 50 to about 600 microseconds.

One or more heartbeat sensors 5 are provided for monitoring the heartbeat of the patient. The sensors 5 are electrically connected via an electrical connection 6 to a recorder/display 7 for recording and/or displaying the patient's heartbeat, preferably in the form of a conventional electrocardiogram or the like. In the embodiment shown, a programmable controller 8 is electrically connected to the signal generator 1 via an electrical connection 9 and to the one or more heartbeat sensors 5 via an electrical connection 10 to the recorder/display 7.

A preferred embodiment of a catheter for use in the inventive system and method is shown generally in FIG. 1. The catheter 10 comprises an elongated catheter body 12 having proximal and distal ends, a intermediate section 14 at the distal end of the catheter body, a control handle 16 at the proximal end of the catheter body, and an electrode assembly 17 mounted at the distal end of the catheter to the intermediate section.

Figure 2:
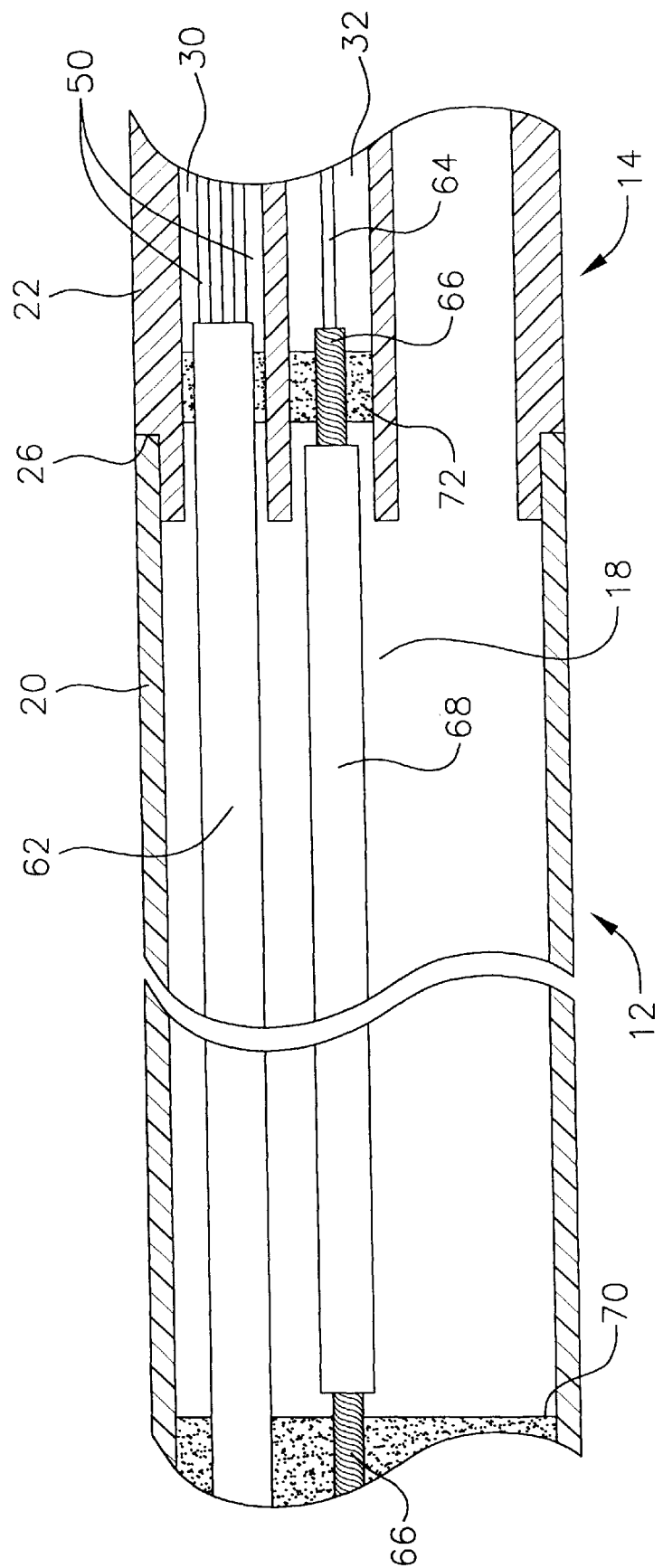
FIG. 2 is a side cross-sectional view of a catheter body according to the invention, including the junction between the catheter body and intermediate section.

With reference to FIG. 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate a puller wire, lead wires, and any other desired wires, cables or tubes. If desired, the inner surface of the outer wall 20 is lined with a stiffening tube (not shown) to provide improved torsional stability. A particularly preferred catheter has an outer wall 20 with an outer diameter of from about 0.090 inch to about 0.94 inch and an inner diameter of from about 0.061 inch to about 0.065 inch.

The intermediate section 14 comprises a short section of tubing 22 having three lumens. The first lumen 30 electrode carries lead wires 50, the second lumen 32 carries a puller wire 64, and the third lumen 34 carries a support member 24. The tubing 22 is made of a suitable non-toxic material that is preferably more flexible than the catheter body 12. A presently preferred material for the tubing 22 is braided polyurethane, i.e., polyurethane with an embedded mesh of braided stainless steel or the like. The size of each lumen is not critical, but is sufficient to house the lead wires, puller wire or support member.

The useful length of the catheter, i.e., that portion that can be inserted into the body excluding the electrode assembly 17, can vary as desired. Preferably the useful length ranges from about 110 cm to about 120 cm. The length of the intermediate section 14 is a relatively small portion of the useful length, and preferably ranges from about 3.5 cm to about 10 cm, more preferably from about 5 cm to about 6.5 cm.

A preferred means for attaching the catheter body 12 to the intermediate section 14 is illustrated in FIG. 2. The proximal end of the intermediate section 14 comprises an outer circumferential notch 26 that receives the inner surface of the outer wall 20 of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

If desired, the catheter body 12 and intermediate section 14 can be formed of a single, unitary tubing, rather than being formed of two separate pieces of tubing that are joined together. Such a design might be desirable, for example, where the catheter body 12 and intermediate section 14 contain the same number of lumens. Accordingly, the term "intermediate section", as used herein, does not require a separate piece of tubing, but instead designates the distal region of the straight, flexible tubing of the catheter.

At the distal end of the intermediate section 14 is a generally circular electrode assembly 17, as shown in FIGS. 3 to 7. In the depicted embodiment, the electrode assembly 17 is formed from the distal end of the support member 24 covered by a non-conductive covering 28. The electrode assembly 17 comprises a generally straight proximal region 38, a generally circular main region 39 and a generally straight distal region 40. The proximal region 38 is mounted on the intermediate section 14, as described in more detail below, so that its axis is generally parallel to the axis of the intermediate section. The proximal region 38 preferably has an exposed length, e.g, not contained within the intermediate section 14, ranging from about 3 mm to about 12 mm, more preferably about 3 mm to about 8 mm, still more preferably about 5 mm inch, but can vary as desired.

Figure 4:
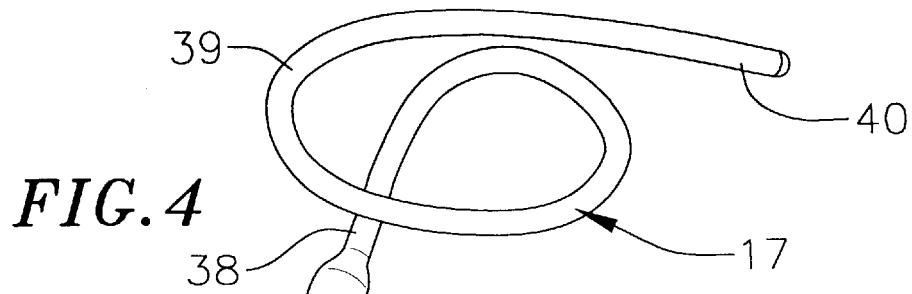
FIG. 4 is a schematic perspective view of the electrode assembly according to the invention.
Figure 5:
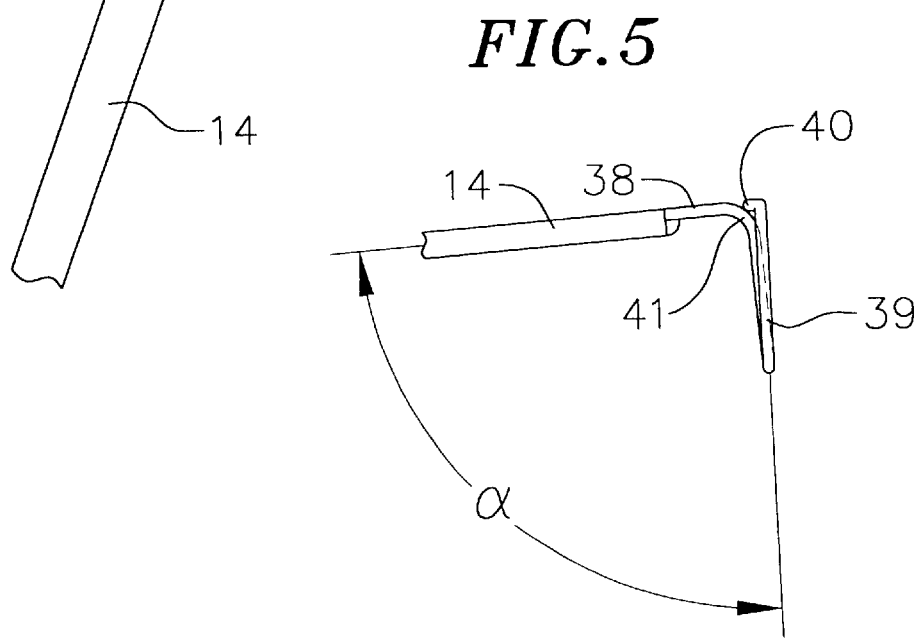
FIG. 5 is a side view of the electrode assembly according to the invention in a clockwise formation.
Figure 6:
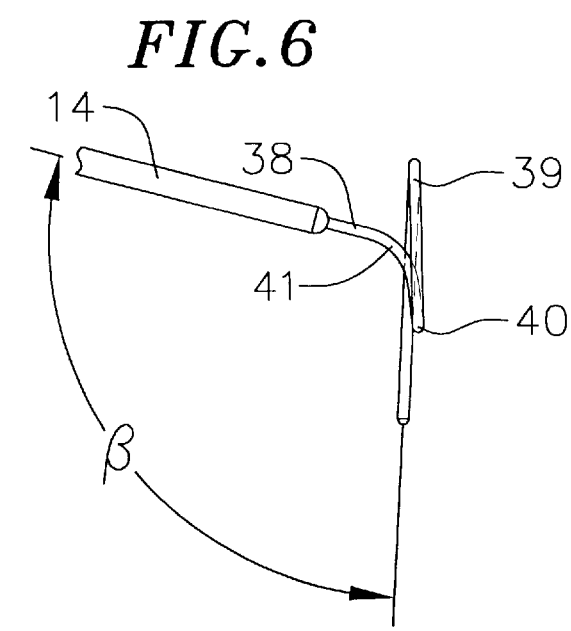
FIG. 6 is a side view of the electrode assembly according to the invention in a counterclockwise formation rotated 90° relative to the assembly depicted in FIG. 5.

The generally circular main region 39 does not form a flat circle, but is very slightly helical, as shown in FIGS. 4 to 6. The main region 39 has an outer diameter preferably ranging from about 10 mm to about 25 mm, more preferably from about 12 mm to about 20 mm, still more preferably about 15 mm. A transition region 41 joins the straight proximal region 38 and generally circular main region 39. The transition region 41 is slightly curved and formed such that, when viewed from the side with the proximal region 38 at the top of the generally circular main region 39 as shown in FIG. 5, the proximal region (along with the intermediate section 14) forms an angle α with the curved region ranging from about 75° to about 95°, preferably from about 83° to about 93°, more preferably about 87°. The main region 39 can curve in a clockwise direction, as shown in FIG. 5, or a counterclockwise direction, as shown in FIG. 6. When the electrode assembly 17 is turned 90°, as shown in FIG. 6, so that the transition region 41 is near the center of the main region 39, the proximal region 38 (along with the intermediate section 14) forms an angle β with the main region ranging from about 90° to about 135°, preferably from about 100° to about 110°, more preferably about 105°.

The support member 24 is preferably made of a material having shape-memory, i.e., that can be straightened or bent out of its original shape upon exertion of a force and is capable of substantially returning to its original shape upon removal of the force. A particularly preferred material for the support member 24 is a nickel/titanium alloy. Such alloys typically comprise about 55% nickel and 45% titanium, but may comprise from about 54% to about 57% nickel with the balance being titanium. A preferred nickel/titanium alloy is nitinol, which has excellent shape memory, together with ductility, strength, corrosion resistance, electrical resistivity and temperature stability. The non-conductive covering 28 can be made of any suitable material, and is preferably made of a biocompatible plastic such as polyurethane or PEBAX. If desired, the support member 24 can be eliminated, for example, if the non-conductive covering 28 is made of a material capable of being straightened with force and returning to a curved shape upon removal of the force.

A series of ring electrodes 36 are mounted on the non-conductive covering 28 of the generally circular main region 39 of the electrode assembly 17. The ring electrodes 36 can be made of any suitable solid conductive material, such as platinum or gold, preferably a combination of platinum and iridium, and mounted onto the non-conductive covering 28 with glue or the like. Alternatively, the ring electrodes can be formed by coating the non-conductive covering 28 with an electrically conducting material, like platinum, gold and/or iridium. The coating can be applied using sputtering, ion beam deposition or an equivalent technique.

In a preferred embodiment, each ring electrode 36 is mounted by first forming a hole in the non-conductive covering 28. An electrode lead wire 50 is fed through the hole, and the ring electrode 36 is welded in place over the lead wire and non-conductive covering 28. The lead wires 50 extend between the non-conductive covering 28 and the support member 24. The proximal end of each lead wire 50 is electrically connected to a suitable connector 37, which is connected to a source of RF energy (not shown).

Figure 7:
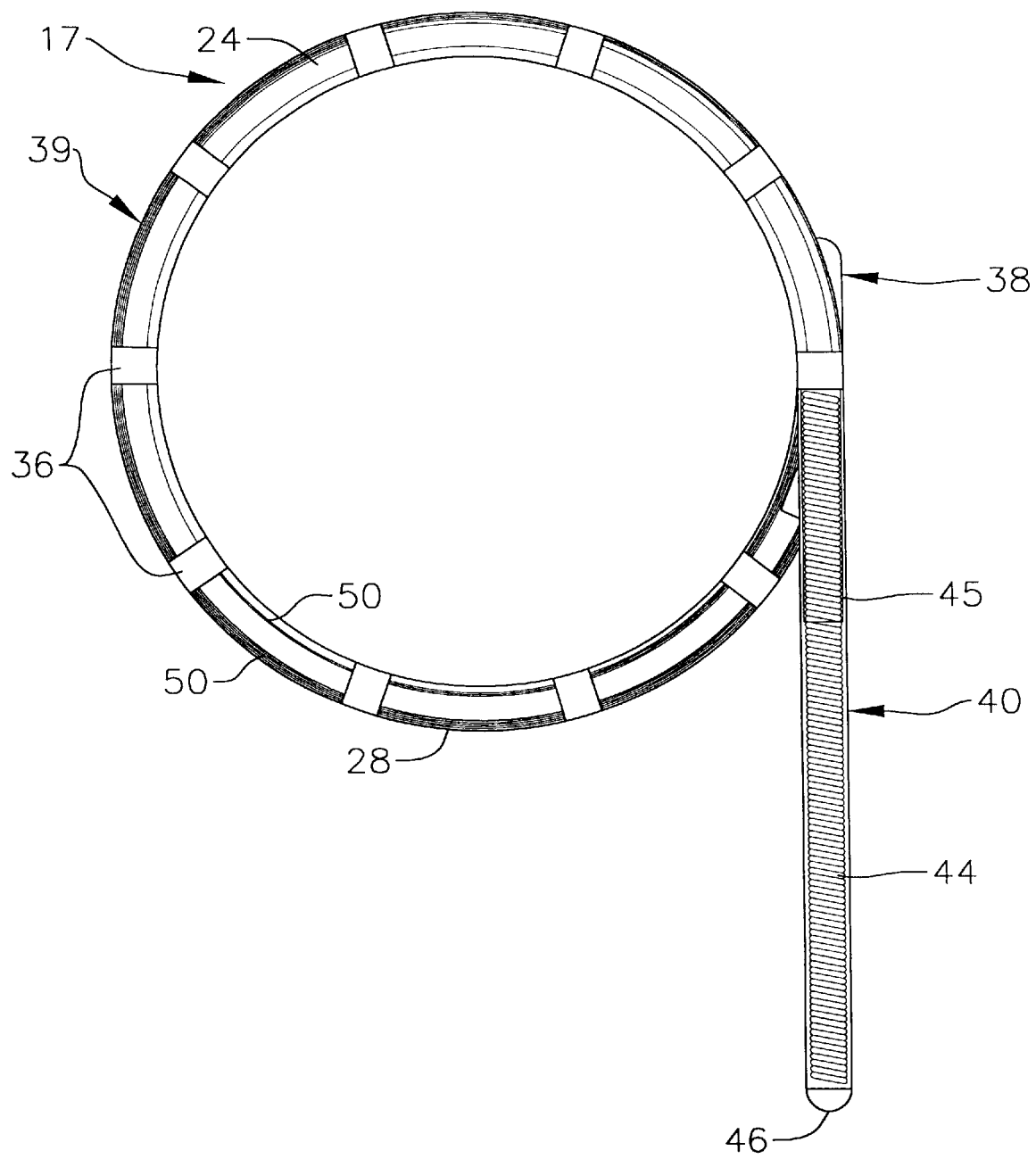
FIG. 7 is a schematic view of the electrode assembly according to the invention.

The number of ring electrodes 36 on the electrode assembly 17 can vary as desired. Preferably the number of ring electrodes ranges from about six to about twenty, more preferably from about eight to about twelve. In a particularly preferred embodiment, the electrode assembly carries ten ring electrodes. The ring electrodes 36 are preferably approximately evenly spaced around the generally circular main region 39, as best shown in FIG. 7. In a particularly preferred embodiment, a distance of approximately 5 mm is provided between the centers of the ring electrodes 36.

Figure 8:
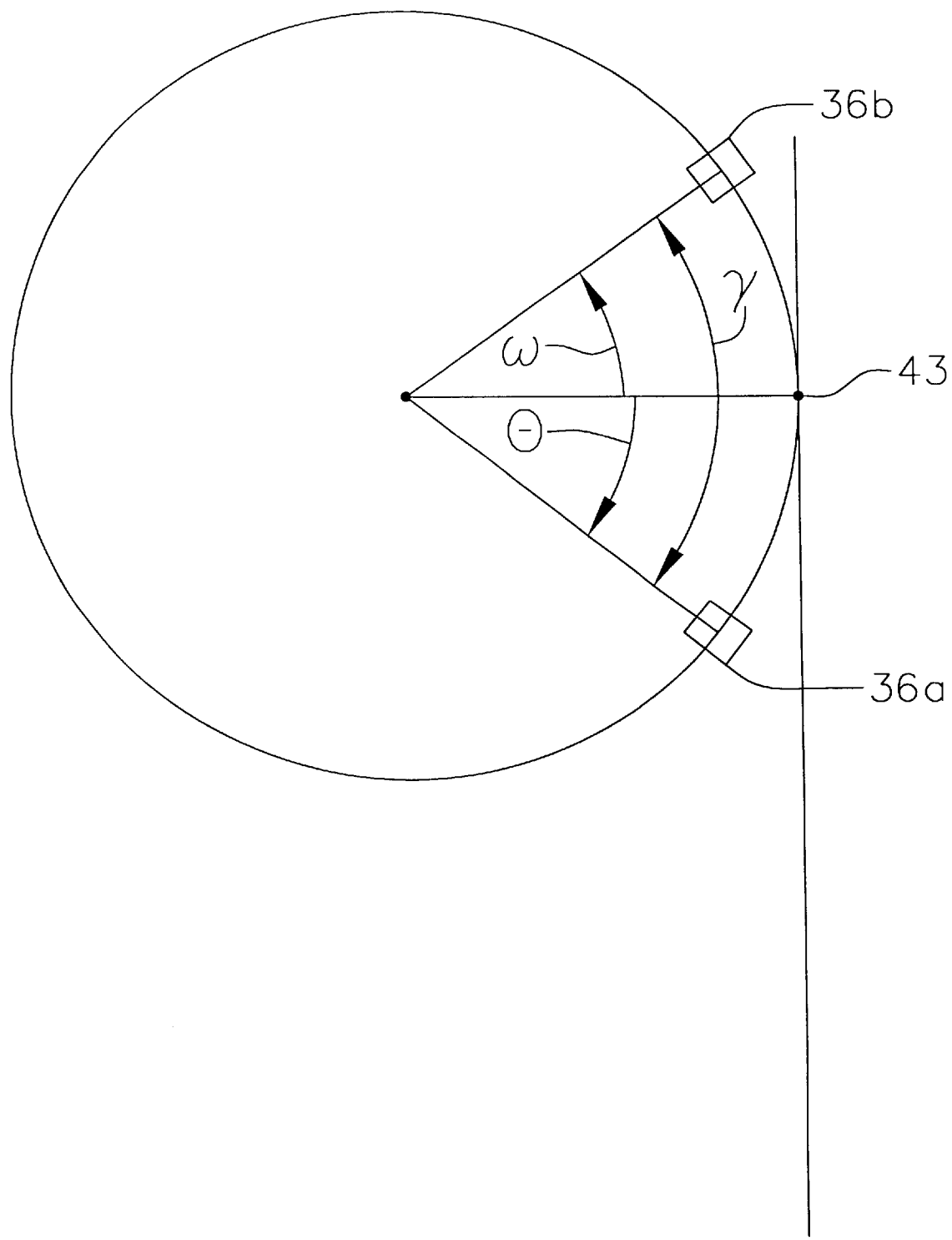
FIG. 8 is a schematic view of the electrode assembly according to the invention depicting the relationship between the first and last electrodes.

FIGS. 7 and 8 show a particularly preferred electrode arrangement. As explained above, the generally circular main region 39 is very slightly helical, although FIGS. 7 and 8 depict the main region as a flat circle, as it would generally appear when viewed from the distal end of the catheter. The generally straight distal region 40 forms a tangent relative to the generally circular main region 39 and contacts the main region at a tangent point 43. A first electrode 36a is provided, which is the electrode that is on the generally circular main region 39 closest to the proximal region 38. A second electrode 36b is provided, which is the electrode that is on the generally circular main region 39 closest to the distal region 40. Preferably, the first electrode 36a is positioned along the circumference of the generally circular main region 39 at a distance θ of no more than about 55° from the tangent point, more preferably no more than about 48° from the tangent point, still more preferably from about 15° to about 36° from the tangent point. Preferably the second electrode 36b is positioned along the circumference of the generally circular main region 39 at a distance ω of no more than about 55° degrees from the tangent point, more preferably no more than about 48° from the tangent point, still more preferably from about 15° to about 36° from the tangent point. Preferably the first electrode 36a is positioned along the circumference of the generally circular main region 39 at a distance γ of no more than about 100° from the second electrode 36b, preferably no more than 80° from the second electrode, still more preferably from about 30° to about 75° from the second electrode.

If desired, additional electrodes (not shown) could be mounted along the intermediate section 14, the generally straight proximal section 39, the transition region 41, and/or the generally straight distal region 40.

In a preferred embodiment, the generally straight distal region 40 is provided with an atraumatic design to prevent the distal end of the electrode assembly 17 from penetrating tissue. In the depicted embodiment, the distal region 40 comprises a tightly wound coil spring 44 made, for example, of stainless steel, such as the mini guidewire commercially available from Cordis Corporation (Miami, Fla.) or a coil having a 0.0045 inch wire size and a 0.009 inch inner diameter. The coil spring 44 is mounted at its proximal end in a short piece of tubing 45 with polyurethane glue or the like, which is then glued or otherwise anchored within the non-conductive covering 28. The tubing 45 is less flexible than the non-conductive covering 28 but more flexible than the support member 24 to provide a transition in flexibility along the length of the electrode assembly 17. The distal end of the distal region 40 is capped, preferably with polyurethane glue 46, to prevent body fluids from entering the electrode assembly 17.

In the depicted embodiment, the generally straight distal region 40 has a length of about 0.5 inch, but can be any desired length, for example, ranging from about 0.25 inch to about 1.0 inch. The generally straight distal region 40 is preferably sufficiently long to serve as an anchor for introducing the catheter into a guiding sheath, as discussed in more detail below, because the generally circular electrode assembly 17 must be straightened upon introduction into the sheath. Without having the generally straight distal region 40 as an anchor, the generally circular electrode assembly 17 has a tendency to pull out of the guiding sheath upon its introduction into the guiding sheath. Additionally, if desired, the distal region 40 can be formed, at least in part, of a radiopaque material to aid in the positioning of the electrode assembly 17 under fluoroscopy.

Figure 3:
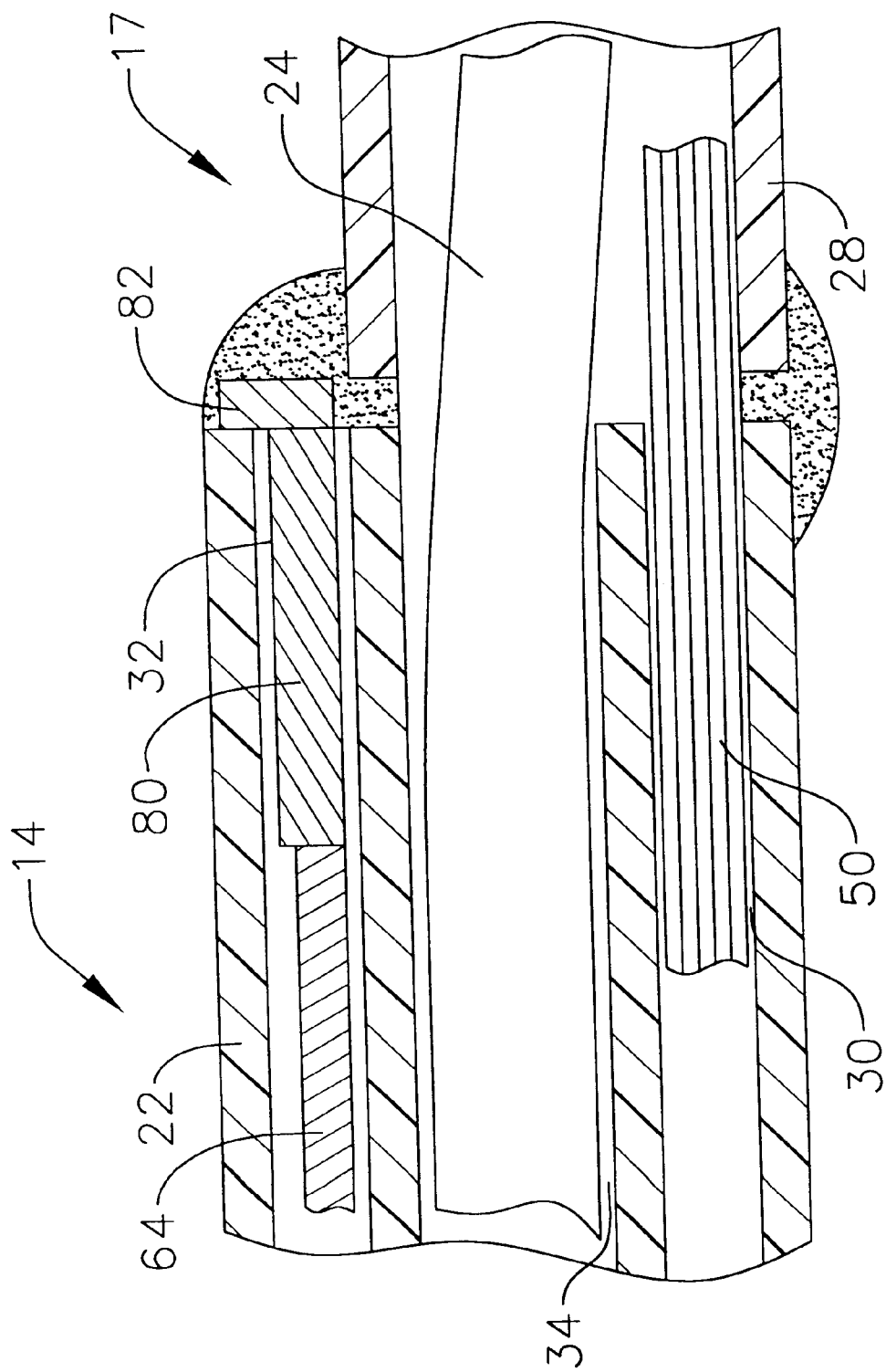
FIG. 3 is a cross-sectional view of the intermediate section, including the junction between the intermediate section and the electrode assembly.

The junction of the intermediate section 14 and electrode assembly 17 is shown in FIG. 3. The non-conductive covering 28 is attached to the tubing 22 of the intermediate section 14 by glue or the like. The support member 24 extends from the third lumen 32 into the non-conductive covering 28. In the depicted embodiment, the proximal end of the support member 24 terminates a short distance within the third lumen 32, approximately about 5 mm, so as not to adversely affect the ability of the intermediate section 14 to deflect. However, if desired, the proximal end of the support member 24 can extend into the catheter body 12.

The lead wires 50 attached to the ring electrodes 36 extend through the first lumen 30 of the intermediate section 14, through the central lumen 18 of the catheter body 12, and the control handle 16, and terminate at their proximal end in the connector 37. The portion of the lead wires 50 extending through the central lumen 18 of the catheter body 12, control handle 16 and proximal end of the intermediate section 14 are enclosed within a protective sheath 62, which can be made of any suitable material, preferably polyimide. The protective sheath 62 is anchored at its distal end to the proximal end of the intermediate section 14 by gluing it in the first lumen 30 with polyurethane glue or the like.

The puller wire 64 is provided for deflection of the intermediate section 14. The puller wire 64 extends through the catheter body 12, is anchored at its proximal end to the control handle 16, and is anchored at its distal end to the intermediate section 14. The puller wire 64 is made of any suitable metal, such as stainless steel or Nitinol, and is preferably coated with Teflon® or the like. The coating imparts lubricity to the puller wire 64. The puller wire 64 preferably has a diameter ranging from about 0.006 to about 0.010 inch.

A compression coil 66 is situated within the catheter body 12 in surrounding relation to the puller wire 64. The compression coil 66 extends from the proximal end of the catheter body 12 to the proximal end of the intermediate section 14. The compression coil 66 is made of any suitable metal, preferably stainless steel. The compression coil 66 is tightly wound on itself to provide flexibility, i.e., bending, but to resist compression. The inner diameter of the compression coil 66 is preferably slightly larger than the diameter of the puller wire 64. The Teflon® coating on the puller wire 64 allows it to slide freely within the compression coil 66. The outer surface of the compression coil 66 is covered by a flexible, non-conductive sheath 68, e.g., made of polyimide tubing.

The compression coil 66 is anchored at its proximal end to the outer wall 20 of the catheter body 12 by proximal glue joint 70 and at its distal end to the intermediate section 14 by distal glue joint 72. Both glue joints 70 and 72 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 20 of the catheter body 12 which is heated sufficiently to form a permanent hole. The glue is then introduced through the hole to the outer surface of the compression coil 66 and wicks around the outer circumference to form a glue joint about the entire circumference of the compression coil.

The puller wire 64 extends into the second lumen 32 of the intermediate section 14. Preferably the puller wire 64 is anchored at its distal end to the distal end of the intermediate section 14, as shown in FIG. 3. Specifically, a T-shaped anchor is formed, which comprises a short piece of tubular stainless steel 80, e.g., hypodermic stock, which is fitted over the distal end of the puller wire 64 and crimped to fixedly secure it to the puller wire. The distal end of the tubular stainless steel 80 is fixedly attached, e.g., by welding, to a cross-piece 82 formed of stainless steel ribbon or the like. The cross-piece 82 sits beyond the distal end of the second lumen 32. The cross-piece 82 is larger than the lumen opening and, therefore, cannot be pulled through the opening. The distal end of the second lumen 32 is then filled with glue or the like, preferably a polyurethane glue. Within the second lumen 32 of the intermediate section 14, the puller wire 64 extends through a plastic, preferably Teflon®, puller wire sheath (not shown), which prevents the puller wire 64 from cutting into the wall of the intermediate section 14 when the intermediate section is deflected.

Longitudinal movement of the puller wire 42 relative to the catheter body 12, which results in deflection of the intermediate section 14, is accomplished by suitable manipulation of the control handle 16. Examples of suitable control handles for use in the present invention are disclosed, for example, in U.S. Pat. No. Re 34,502 and U.S. Pat. No. 5,897,529, the entire disclosures of which are incorporated herein by reference. As would be recognized by one skilled in the art, other handles capable of longitudinally moving the puller wire could also be used. Depending on the desired application, the deflection mechanism (e.g., control handle, puller wire and compression coil) can be eliminated.

If desired, two or more puller wires can be provided to enhance the ability to manipulate the intermediate section. In such an embodiment, a second puller wire and a surrounding second compression coil extend through the catheter body and into an additional off-axis lumen in the intermediate section. The first puller wire is preferably anchored proximal to the anchor location of the second puller wire. Suitable designs of catheters having two or more puller wires, including suitable control handles for such embodiments, are described, for example, in U.S. Pat. Nos. 6,123,699, 6,171,277, and 6,183,463, and allowed U.S. patent application Ser. No. 09/157,055, filed Sep. 18, 1998, the disclosures of which are incorporated herein by reference.

In use, a suitable guiding sheath is inserted into the patient with its distal end positioned at a desired pacing or ablation location. An example of a suitable guiding sheath for use in connection with the present invention is the Preface™ Braiding Guiding Sheath, commercially available from Cordis Webster (Diamond Bar, Calif.). While it is presently preferred to use a guiding sheath, if the catheter comprises a mechanism for extending and retracting the generally circular electrode assembly 17, a guiding sheath may not be required.

To reach the desired intravascular location, the catheter and guiding sheath are inserted into a blood vessel and then guided to the desired site. During this procedure, the intermediate section 14 may be deflected as needed by manipulation of the puller wire 64. Once the distal ends of the catheter 10 and guiding sheath (not shown) reach the desired location, the guiding sheath is withdrawn, thereby exposing the electrode assembly 17.

Once the electrode assembly 17 is at the desired location, the controller 8 activates the signal generator 1 to transmit signals sequentially to each of the ring electrodes 36 on the main region 39 of the electrode assembly 17 and to determine, based on signals received from the sensors 5 (indicating a response by the heart to the transmitted signals) which of the ring electrodes is closest to the nerve. If there is no response by the heart, the controller 8 activates the signal generator 1 to transmit a second signal sequentially to each of the ring electrodes 36, the second signal being different from the first signal in intensity, frequency and/or duration, preferably intensity. The controller 8 continues this process until a response by the heart is received and the ring electrode(s) 36 closest to the nerve in question is identified. If, after a select period of time, no response from the heart is sensed, the controller 8 provides a signal, e.g., audible or visual, to the physician indicating that the ring electrode(s) 36 are not sufficiently close to the desired nerve and that the catheter needs to be repositioned.

Once the ring electrode(s) 36 nearest the desired nerve have been identified, the controller 8 activates the signal generator 1 to transmit a stimulating signal to the identified electrode(s). If the response by the heart is insufficient, e.g., not enough slowing, the controller 8 activates the signal generator 1 to vary the stimulating signal in one or more of the intensity, frequency and/or pulse duration, preferably in a stepwise fashion, until the desired slowing of the heartbeat rate is achieved. For example, a signal having an intensity sufficient to elicit a response from the heart may slow the heartbeat rate to some degree but not as much as is desired. Accordingly, the signal may be increased stepwise in intensity until the desired amount of slowing is achieved.

The parasympathetic nervous system produces its cardiac action primarily via vagal nerve fibers leading to cardiac ganglia. Sympathetic nerve fibers emerge from multiple cervical and paravertebral ganglia to provide a network of postganglionic nerve endings to the atria, ventricles, sinus node, and atrioventricular node. The terms "nerve" and "nerve fiber" as used herein includes a single neuron, nerve, nerve ending(s), or nerve bundle, and if it is described as "autonomic," may be comprised of all parasympathetic, all sympathetic, or mixed parasympathetic and sympathetic fibers.

Because of the pattern of cardiac autonomic innervation, the invention can be practiced at numerous sites within the vasculature. In fact, any intravascular site that is adjacent to an autonomic fiber that innervates the heart is a potential site for the stimulation method of the invention. As used herein, "intravascular" means within the venous or arterial circulatory system, including blood vessels of all descriptions and chambers of the heart. When referring to "intravascular stimulation" in describing the method of the invention, it is meant stimulation from within the circulatory system resulting in (transvascular) stimulation of a tissue of interest. "Transvenous" or "transvascular" means across a blood vessel or across the wall of a cardiac chamber (including the connective, adipose, muscle, neural, and other associated tissue). "Stimulation" means a stimulus, usually electrical, which causes depolarization of a cell or cells, or portion of a cell, contraction, excitation as measured by e.g., calcium or sodium influx into the cell, or an altered membrane potential across a cell.

Appropriate sites for stimulation are those adjacent to cardiac autonomic nerves. Preferably the sites are sufficiently far from myocardial muscle that the muscle is not at risk of contraction during stimulation. However, for some preferred sites, e.g., the coronary sinus, myocardial muscle is adjacent and can be stimulated by the autonomic stimulation. This is rarely a problem when the atria are in fibrillation, because the stimulation is incapable of causing coordinated atrial contraction.

Potential stimulation sites can be initially selected by reference to general anatomy; blood vessels of sufficient diameter for catheter access which are known to have autonomic fibers innervating the heart running nearby or adjacent are suitable candidates. Care must be taken, of course, to select locations with nerves that primarily innervate the area of interest so that other innervated areas are not affected. For example, three preferred intravascular parasympathetic sites at which a substantial reduction in ventricular rate during atrial fibrillation can be obtained are the ostium of the coronary sinus, the right pulmonary artery and the superior vena cava. Sympathetic bundles may be stimulated from discrete sites, for example, transvascularly from the aorta or the main pulmonary artery to the sympathetic fibers that run alongside. As will be apparent to one of skill in the art, the invention is not limited to sites directly adjacent to the heart, but can be practiced at any of the variety of sites (primarily thoracic) where blood vessels suitable for catheter access run parallel to or otherwise intersect with autonomic fibers serving the heart. Target fibers can thus be accessed from different sites on the patient, for example from near the subclavian, jugular, or azygous veins.

In accordance with the method of the invention, the catheter is introduced into a blood vessel and is guided by suitable means to a desired location. For example, fluoroscopic imaging can be used to guide the catheter to the selected site. In addition or alternatively, if the desired site is close to or within the myocardium, an electrode of the catheter may be used to sense electrical activity of the heart, such that when signals generated by the contraction of the cardiac muscle are detected, the sensing electrode is in the atrium. The catheter may then be advanced through the heart or withdrawn to reach the desired site. If the target site is just outside the heart, the catheter may be advanced or withdrawn until no myocardial contraction is detected. For example, if the target is the right pulmonary artery, the catheter would be advanced through the atrium, the tricuspid valve, and the right ventricle before exiting the heart and entering the right pulmonary artery. When contraction of the heart is no longer sensed, the catheter would be in a suitable position to begin testing for the desired stimulation location. Likewise, if the target is the superior vena cava, for example, sensing is performed from the catheter until atrial impulses are detected, indicating that the catheter is in the atrium. From that point, the catheter is slowly withdrawn until atrial signals are no longer detected. This would indicate that the catheter is in the superior vena cava.

Stimulation can be optimized by varying the intensity, frequency, polarity, and/or pulse duration of the signal. Of particular usefulness is changing the signal strength. A graded response of the ventricular rate during atrial fibrillation ranging from slight slowing to complete AV block can be accomplished. The desired level will be somewhere in between these extremes, and will vary depending on the patient's condition. Parameters and protocols for nerve stimulation can be any that produce the desired sympathetic or parasympathetic effects on the heart, and can be adjusted as needed for different patients or during an individual patient's treatment.

In general, stimulus pulse duration, amplitude, polarity, and/or intensity can be modified. The pulse duration can range from about 1 microsecond to about 10 milliseconds, preferably about 100 $\mu$sec (0.1 ms); the frequency will be from about 1 to about 200 Hz, preferably from about 20–45 Hz; and the stimulus intensity will be from about 1 to about 150 V, preferably from about 8 to about 15 V. Frequencies from about 20 to about 45 Hz have been found to achieve the most preferable supraventricular rate slowing. The optimum signal will depend on the current density achieved at the stimulation site, the voltage drop across the stimulating equipment to the delivery site, and other factors well known to those of skill in the art. Lower voltages and frequencies are generally preferred, since they reduce the risk of tissue damage or any possible discomfort in patients arising from the stimulation. Shorter duration pulses are generally preferred because they reduce the possibility of depolarizing nearby muscle fibers.

If the selected stimulation site is adjacent to cardiac muscle, contraction of the muscle in response to the nerve stimulation can be avoided by timing the stimuli to coincide with the myocardial refractory period (when no amount of stimulation will induce contraction of the muscle). If this is done, a stronger signal may be used. If desired, concurrent pacing of the atria or ventricles can be performed to time the nerve stimulation to the heartbeat or refractory period of the muscle. Concurrent pacing can be performed with the same or a different catheter or electrode(s), and can be within the heart or vasculature or externally using any known methods. Likewise, recording or monitoring can be accomplished with the same or different electrodes or catheters.

The system and methods of the invention can be used to ablate sympathetic and parasympathetic nerves if necessary. Sympathectomy is indicated in certain patients, for example those with contraindications to β-blockers. Selective sympathetic denervation, performed by transvascular ablation using the method of the invention, can reduce these patients' risk of sudden death from acute arrhythmias. Selective parasympathetic denervation may be indicated in patients with atrial tachycardia or fibrillation induced or maintained by excessive vagal nerve stimulation. A denaturing or ablating stimulus (e.g., radio frequency or cryoablation) is applied across the vessel wall to the sympathetic fibers at any desired location. Preferably sites are selected where a purely or nearly pure sympathetic or parasympathetic branch runs very close to the vessel and where there are few other nerves or other sensitive tissues. Ablating stimulation is applied until conduction in the fiber is impaired or ceases altogether. This can be monitored by any means, including recording from the heart to observe a change in heart rate. Such ablation is irreversible, and can be very selectively performed by first stimulating the nerve to determine its innervation sites and selecting an ablation location that maximizes the desired effect while minimizing unwanted ablation.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A method for regulating the heart rate of a patient comprising:
    inserting into a blood vessel of the patient a catheter having an electrode assembly at its distal end, the electrode assembly having a continuous generally circular main region comprising a generally circular non-conductive covering that is generally transverse to the axis of the catheter and on which is mounted at least one electrode;
    directing the catheter to an intravascular location wherein the at least one electrode on the electrode assembly is adjacent to a selected cardiac sympathetic or parasympathetic nerve;
    stabilizing the at least one electrode at the intravascular location; and
    delivering a stimulus through the at least one electrode, the stimulus being selected to stimulate the adjacent sympathetic or parasympathetic nerve to thereby cause a regulation of the patient's heart rate.

2. The method of claim 1, wherein the stimulation causes a slowing of the heart rate.

3. The method of claim 2, wherein the patient is suffering from atrial or ventricular tachycardia.

4. The method of claim 2, wherein the patient is suffering from atrial flutter.

5. The method of claim 2, wherein the patient is suffering from atrial fibrillation.

6. The method of claim 1, wherein the intravascular location is selected from the group consisting of the coronary sinus, the right pulmonary artery, and the superior vena cava.

7. The method of claim 1, wherein the electrode assembly comprises a support member having shape memory surrounded by the non-conductive covering.

8. The method of claim 7, wherein the electrode assembly carries a plurality of electrodes on the non-conductive covering.

9. The method of claim 1, wherein the electrode assembly further comprises a generally straight proximal region proximal to the generally circular main region, a transition region connecting the proximal region and the main region, and a generally straight distal region distal to the main region.

10. The method of claim 9, wherein the electrode assembly further comprises a support member having shape-memory disposed within at least the main region of the electrode assembly.

11. The method of claim 9, wherein the transition region is slightly curved and formed such that, when viewed from the side of the catheter with the proximal region at the top of the circular main region, the proximal region forms an angle α with the circular region ranging from about 75° to about 95°.

12. The method of claim 9, wherein the generally straight distal region has an atraumatic design to prevent the distal end of the electrode assembly from penetrating tissue.

13. The method of claim 9, wherein the generally straight distal region has a length ranging from about 0.25 inch to about 1.0 inch.

14. The method of claim 1, wherein the generally circular main region has an outer diameter ranging from about 10 mm to about 25 mm.

15. The method of claim 1, wherein the generally circular main region has an outer diameter ranging from about 12 mm to about 20 mm.

16. The method of claim 1, wherein the electrode assembly carries a plurality of electrodes that are approximately evenly spaced around the generally circular main region.

17. The method of claim 1, wherein the stimulus comprises one or more electrical signals having a frequency of from about 1 Hz to about 200 Hz, an intensity of from about 1 V to about 150 V and a duration of from about 0.01 msec to about 10 msec.

18. The method of claim 17, wherein the frequency of the electrical signal(s) ranges from about 20 Hz to about 30 Hz.

19. The method of claim 17, wherein the intensity of the electrical signal(s) is from about 8 V to about 15 V.

20. The method of claim 17, wherein the duration of the electrical signal(s) is from about 0.05 msec to about 0.1 msec.

21. The method of claim 1, wherein the stimulation is timed to occur during a myocardial refractory period.

22. The method of claim 21, wherein the refractory period is regulated by myocardial pacing.

23. The method of claim 22, wherein the myocardial pacing is elicited from the at least one electrode or a second electrode on the catheter.

24. A method of selectively ablating a sympathetic or parasympathetic innervation of at least one portion of the heart of a patient comprising:
    inserting into a blood vessel of the patient a catheter having an electrode assembly at its distal end, the electrode assembly having a continuous generally circular main region comprising a generally circular non-conductive covering that is generally transverse to the axis of the catheter and on which is mounted at least one electrode;
    directing the catheter to an intravascular location wherein the at least one electrode on the electrode assembly is adjacent to a selected cardiac sympathetic or parasympathetic nerve;
    stabilizing the electrode at the intravascular location; and
    delivering an ablation stimulus through the electrode, the ablating stimulus being sufficient to damage the nerve so that it no longer conducts impulses to the heart.

25. The method of claim 24, wherein the electrode assembly comprises a support member having shape memory surrounded by the non-conductive covering.

26. The method of claim 25, wherein the electrode assembly carries a plurality of electrodes on the non-conductive covering.

27. The method of claim 24, wherein the electrode assembly further comprises a generally straight proximal region proximal to the generally circular main region, a transition region connecting the proximal region and the main region, and a generally straight distal region distal to the main region.

28. The method of claim 27, wherein the transition region is slightly curved and formed such that, when viewed from the side of the catheter with the proximal region at the top of the circular main region, the proximal region forms an angle α with the circular region ranging from about 75° to about 95°.

29. The method of claim 24, wherein the generally circular main region has an outer diameter ranging from about 10 mm to about 25 mm.

30. The method of claim 24, wherein the generally circular main region has an outer diameter ranging from about 12 mm to about 20 mm.

31. The method of claim 24, wherein the electrode assembly carries a plurality of electrodes that are approximately evenly spaced around the generally circular main region.

32. A system to regulate the heart rate of a patient comprising:

a catheter having an electrode assembly at its distal end, the electrode assembly having a generally circular main region comprising a continuous generally circular non-conductive covering that is generally transverse to the axis of the catheter and on which is mounted at least one electrode; and a signal generator electrically connected to the at least one electrode on the generally circular main region, the signal generator being capable of generating stimulating pulses having a frequency of from about 1 Hz to about 200 Hz, an intensity of from about 1V to about 200 V and a duration of from about 0.01 msec to about 10 msec.

33. The system of claim 32, wherein the electrode assembly comprises a support member having shape memory surrounded by the non-conductive covering.

34. The system of claim 33, wherein the electrode assembly carries a plurality of electrodes on the non-conductive covering.

35. The system of claim 32, wherein the electrode assembly further comprises a generally straight proximal region proximal to the generally circular main region, a transition region connecting the proximal region and the main region, and a generally straight distal region distal to the main region.

36. The system of claim 35, wherein the electrode assembly further comprises a support member having shape-memory disposed within at least the main region of the electrode assembly.

37. The system of claim 35, wherein the transition region is slightly curved and formed such that, when viewed from the side of the catheter with the proximal region at the top of the circular main region, the proximal region forms an angle $\alpha$ with the circular region ranging from about 75° to about 95°.

38. The system of claim 35, wherein the generally straight distal region has an atraumatic design to prevent the distal end of the electrode assembly from penetrating tissue.

39. The system of claim 35, wherein the generally straight distal region has a length ranging from about 0.25 inch to about 1.0 inch.

40. The system of claim 32, wherein the generally circular main region has an outer diameter ranging from about 10 mm to about 25 mm.

41. The system of claim 32, wherein the generally circular main region has an outer diameter ranging from about 12 mm to about 20 mm.

42. The system of claim 32, wherein the electrode assembly carries a plurality of electrodes that are approximately evenly spaced around the generally circular main region.

* * * * *

UNITED STATES PATENT AND TRADEMARK OFFICE
CERTIFICATE OF CORRECTION

PATENT NO. : 6,564,096 B2
DATED : May 13, 2003
INVENTOR(S) : Mest

It is certified that error appears in the above-identified patent and that said Letters Patent is hereby corrected as shown below:

Title page,
Item [56], References Cited, OTHER PUBLICATIONS,
"Neural Effects on Sinus…" reference, replace "of" with -- from --.
"M. Haussaguerre et al.," reference, replace "Ectoic" with -- Ectopic --.
"Murphy, DA, et al," reference, replace "1995" with -- 1985 --.
"Chen, SA, et al." reference, replace "Dromotroic" with -- Dromotropic --.
"Leenhardt, A., et al.," reference, replace "Catecholainergic" with
-- Catecholaminergic --.
"Tsai, C., et al.," reference, before "Pulmonary" insert -- the --; and after "Journal of" delete "the".
"Scherlag, B.J., et al." reference, replace "Arium" with -- Atrium --.
Insert the following:
-- Haissaguerre, M., *Radiofrequency Catheter Ablation in Unusual Mechanisms of Atrial Fibrilation: Report of Three Cases*, Journal of Cardiovascular Electrophysiology, Vol. 5, No. 9, Sept. 1994, pgs. 743-751. --.
-- Fuimaono, K., et al., *Catheter Having Mapping Assembly*, U.S. Application No. 09/551,467; Filed April 17, 2000; W112:37312. --.
-- Fuimaono, K., et al., *Catheter Having Mapping Assembly*, U.S. Application No. 09/943,546; Filed August 30, 2001; W112:47022. --.
-- Coleman, J., et al., *Bidirectional Catheter Having Mapping Assembly*, U.S. Application No. 10/107,899; Filed March 25, 2002; W112:45950. --.

Signed and Sealed this

Twenty-ninth Day of November, 2005

JON W. DUDAS
*Director of the United States Patent and Trademark Office*